(12) United States Patent
Wennergren et al.

(10) Patent No.: US 9,302,221 B2
(45) Date of Patent: Apr. 5, 2016

(54) METHOD FOR UPGRADING A GAS

(71) Applicant: RE-N TECHNOLOGY APS, Lejre (DK)

(72) Inventors: Bo Wennergren, Lund (SE); Jens Tradsborg Christensen, Stockholm (SE)

(73) Assignee: RE-N TECHNOLOGY APS, Lejre (DK)

( * ) Notice: Subject to any disclaimer, the term of this patent is extended or adjusted under 35 U.S.C. 154(b) by 23 days.

(21) Appl. No.: 14/346,125

(22) PCT Filed: Jan. 2, 2013

(86) PCT No.: PCT/DK2013/000001
§ 371 (c)(1),
(2) Date: Mar. 20, 2014

(87) PCT Pub. No.: WO2013/104364
PCT Pub. Date: Jul. 18, 2013

(65) Prior Publication Data
US 2014/0241968 A1  Aug. 28, 2014

(30) Foreign Application Priority Data

Dec. 22, 2011 (DK) .................................. 2011 00994
Dec. 21, 2012 (WO) ................ PCT/DK2012/050506

(51) Int. Cl.
| | |
|---|---|
| *B01D 53/62* | (2006.01) |
| *B01D 53/02* | (2006.01) |
| *C07C 7/12* | (2006.01) |
| *B01D 53/04* | (2006.01) |
| *B01D 53/047* | (2006.01) |
| *B01D 53/80* | (2006.01) |

(52) U.S. Cl.
CPC .............. *B01D 53/62* (2013.01); *B01D 53/025* (2013.01); *C07C 7/12* (2013.01); *B01D 53/047* (2013.01); *B01D 53/0462* (2013.01); *B01D 53/80* (2013.01); *B01D 2253/206* (2013.01); *B01D 2257/504* (2013.01); *Y02C 10/04* (2013.01); *Y02C 10/08* (2013.01); *Y02C 20/20* (2013.01)

(58) Field of Classification Search
CPC ........ Y02C 10/08; Y02C 10/04; B01D 53/62; C07C 7/12
See application file for complete search history.

(56) References Cited

U.S. PATENT DOCUMENTS

| | | | |
|---|---|---|---|
| 3,627,478 A * | 12/1971 | Tepper .......................... | 423/230 |
| 2005/0160913 A1 | 7/2005 | Hrycak | |
| 2011/0088550 A1 * | 4/2011 | Tirio ................................. | 95/96 |
| 2015/0165372 A1 * | 6/2015 | Schenker et al. ...... | B01D 53/62 |

FOREIGN PATENT DOCUMENTS

| | | |
|---|---|---|
| GB | 1 296 889 A | 11/1972 |
| WO | 2011/049759 A1 | 4/2011 |

OTHER PUBLICATIONS

International Search Report of PCT/DK2013/000001 dated Apr. 23, 2013.

* cited by examiner

*Primary Examiner* — Timothy Vanoy
(74) *Attorney, Agent, or Firm* — Sughrue Mion, PLLC

(57) ABSTRACT

The invention relates to a method for upgrading a gas by separation of carbon dioxide therefrom, which method comprises the steps of introducing a stream of gas to a wet bed of ion exchange resin, and desorbing the adsorbed carbon dioxide from the resin by increasing the temperature and/or lowering the pressure in said wet bed.

13 Claims, 1 Drawing Sheet

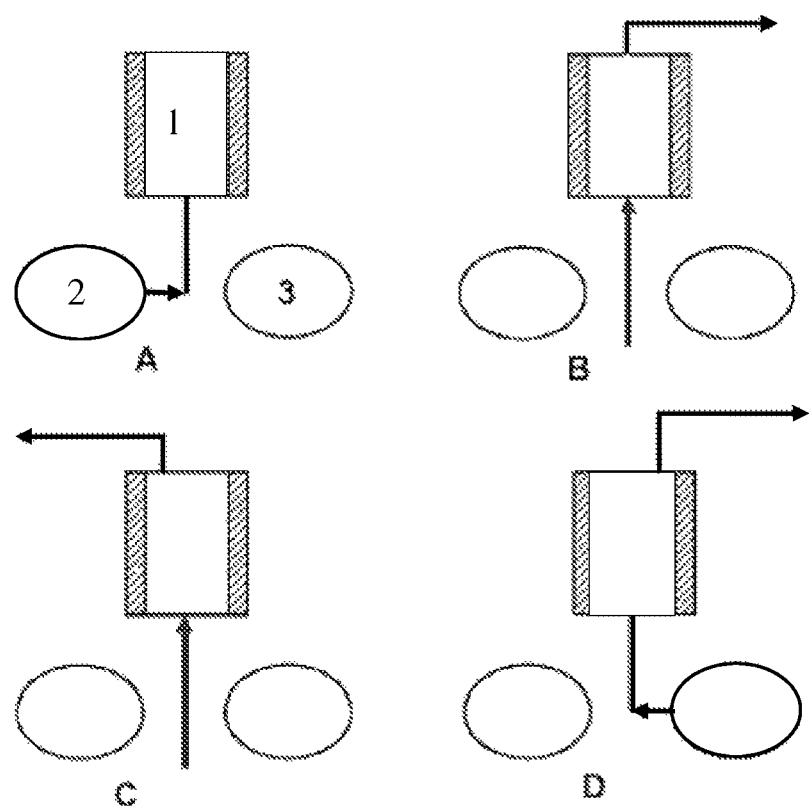

METHOD FOR UPGRADING A GAS

CROSS REFERENCE TO RELATED APPLICATIONS

This is a National Stage of International Application No. PCT/DK2013/000001 filed Jan. 2, 2013, claiming priorities based on Danish Patent Application No. PA 2011 00994 filed Dec. 22, 2011 and International Application No. PCT/DK2012/050506 filed Dec. 21, 2012, the contents of all of which are incorporated herein by reference in their entirety.

BACKGROUND OF THE INVENTION

The present invention relates to a method for upgrading a gas by separation of carbon dioxide therefrom.

Most gases employed for large-scale energy purposes, such as natural gas, town gas, and biogas, present as their main constituent methane. Various other combustibles may also be present, and additionally a certain share of carbon dioxide is normally encountered, which latter compound may com-promise the technical and calorific properties of the gas.

On the other hand, the bulk of flue gases arising from power plants and a range of other sources is typically made up of free nitrogen. Here, carbon dioxide is captured out of climate concerns or to recover it as a valuable product in its own right.

When it comes to the initially mentioned gases for energy purposes, they must be upgraded to a methane content of 95-98% in order to meet the standards required for gaining entrance to the natural gas grid and to be accepted as vehicle fuels. In this regard, carbon dioxide, which, most pronounced in the case of biogas, may constitute as much as 45% of the crude gas and acts to dilute its energy content, must be cleared away to a large extent.

To separate carbon dioxide from methane, various methods have been applied, among which water scrubbing and pressure/temperature swing adsorption are prominent.

Water scrubbing relies on the fact that carbon dioxide is more soluble in water than methane. The absorption process is purely physical. Normally, the gas is pressurised and fed to the bottom of a packed column, while a stream of water is introduced to the top of the column so that the absorption process is operated counter-currently. The spent water typically must be stripped with air in another column in order to desorb the absorbed carbon dioxide.

In the case of flue gas, wherein carbon dioxide normally is to be separated from a bulk of $N_2$ rather than $CH_4$, a favourite absorbent has been mo-noethanol amine (MEA) in stead of water.

Pressure/temperature swing adsorption makes use of adsorbent materi-als, for which carbon dioxide shows a selective affinity. Under pressure or low temperature, carbon dioxide tends to be attracted to certain solid surfaces more strongly than methane. When the pressure is subsequently reduced or the temperature is raised, the carbon dioxide is desorbed and can be re-moved.

The absorption of carbon dioxide in water as in water scrubbing and its adsorption to a solid material during pressure/temperature swing adsorption are generally perceived in the art as two distinct and antagonistic methods to be practiced separately.

For example, the British patent GB 1296889, which discloses a method for separation of carbon dioxide from other gases by temperature swing adsorption to an ion exchange resin, teaches that the resin when adsorbing carbon dioxide should not be wet with unsorbed water as this is believed to hin-der carbon dioxide adsorption. In this regard a content of water in the bed of resin of less than 30% is specified as being desirable.

Likewise, the international patent application WO 2011/049759 de-scribes a method for removing carbon dioxide from a gas stream by temperature and optionally pressure swing adsorption to an ion exchange resin. It is stated that a water content of above 10% by weight in the resin is not bene-ficial and unnecessarily increases regeneration heat requirements.

In the patent application US 2005/0160913 concerning a carbon dioxide absorbent mainly intended for a rebreather system, resort is made to a strongly basic ion exchanger in the form of lithium hydroxide. Said compound is pre-hydrated to form its monohydrate, i.a. to forestall an exothermic reac-tion when in use. When hydrated to a stoichiometric extent, the content of water amounts to approximately 43% by weight. Accordingly, at this level all water is intimately incorporated into LiOH as water of hydration. Thus, no unsorbed water is present, and it is stated that pre-moistening of the ion exchanger beyond this stage is generally undesirable since the solid LiOH would otherwise begin to dissolve and lose its properties.

As adumbrated in the above mention of water scrubbing, a disad-vantage connected to that method is the need for subsequent treatment of the spent water in a separate procedure.

On the other hand, the alternative method of pressure/temperature swing adsorption is not free from incommodi-ties, either. During the phase of its regeneration by pressure and or temperature swing, the adsorbent material obviously is not available for adsorption of carbon dioxide. Accordingly, high demands are set for the adsorption capacity of the adsorbent material and often it must be desorbed too frequently for the method to be operation-ally and economically viable.

SUMMARY OF THE INVENTION

In view of the above, the object of the present invention is to provide an effective, efficient, yet simple and durable procedure for separation of carbon dioxide from a gas, which procedure is environmentally friendly and does not require a continuous supply of extraneous, industrial chemicals.

To meet this object, a method for upgrading or cleaning a gas by separation of carbon dioxide therefrom is provided, which method comprises the steps of introducing a stream of said gas into a bed of a weakly basic ion exchange resin provided with amine groups, at temperature and pressure conditions, under which the carbon dioxide is adsorbed to said resin, and desorbing the adsorbed carbon dioxide from the resin by increasing the temperature and/or lowering the pressure in said bed, wherein the content of water in said bed of ion exchange resin during the step of gas introduction amounts to more than 30%, more than 33% or preferably more than 35% of the total weight of ion exchange resin and water.

It has surprisingly been found that the presence of a considerable amount of unsorbed water in the bed of ion exchange resin do not inhibit clearing of carbon dioxide from the stream of gas to be upgraded, but actual-ly results in an overall capacity for carbon dioxide removal, which is far supe-rior to that achieved by conventionally operated temperature/pressure swing adsorption as well as by water scrubbing.

Hereby, a robust and effective method is provided for upgrading or cleaning a gas, which method furthermore can be performed within a rela-tively modest space.

The employed ion exchange resin preferably is of a macroporous type in order to provide a large surface for adsorption. Its matrix may typically be composed of a polystyrene cross-linked with divinylbenzene. The functional group preferentially is a tertiary amine.

In one embodiment, the gas is a flue gas, which is cleaned by separation of carbon dioxide therefrom. The flue gas may emit from a power plant or any other facility or site, where a stream of waste gas with a content of carbon dioxide is produced. Accordingly, "flue gas" is taken here to designate any type of waste gas.

According to another embodiment, the gas is upgraded by separation of carbon dioxide from methane. As a result of said upgrading, the gas may typically become more suitable for energy purposes.

Depending on the intended end-use as well as the original source of the gas it may be relevant to remove hydrogen sulphide from the crude gas stream prior to its introduction into the bed of ion exchange resin. Oftentimes, this will be required to forestall corrosion of vessels and engines. Methods for hydrogen sulphide removal are well-known within the art.

According to one embodiment, the gas to be treated is natural gas, such as shale gas or other types of fossil gas. In a specific embodiment, the gas is biogas.

Preferably, the content of water in the bed of ion exchange resin during the step of introducing a stream of gas amounts to 37% or more, 40% or more, preferentially 45% or more, advantageously 50% or more, optionally 55% or more, of the total weight of ion exchange resin and water. It has been found that the total capacity for combined adsorption and absorption of carbon dioxide from the stream of gas as well as the adsorption rate culmi-nate close to a water content of 50%.

Advantageously, the content of water in said bed of ion exchange resin during the step of introducing a stream of gas amounts to less than 80%, less than 75%, less than 72%, preferably less than 70%, optionally less than 67%, less than 65% or less than 60% of the total weight of ion exchange resin and water. At water shares exceeding 80%, the mixture of ion exchange resin and water takes on the appearance of a difflu-ent slurry with a layer of resin beads floating atop, and the favourable synergistic effect of $CO_2$-absorption in the water and $CO_2$-adsorption to the ion exchange resin is no longer present.

According to one embodiment of the invention, a flow of water counter to the stream of gas is provided during the step of combined adsorption and absorption, when carbon dioxide is introduced to the bed of ion exchange resin. The flow of water is introduced as a spray above the bed of ion exchange resin, whereas the stream of gas is concomitantly introduced to the bottom of said bed. The produced counter-flow of water emulates the princi-ple of a water-scrubber and has a certain effect in absorbing and driving downwards residual carbon dioxide that passes through the wet bed of ion exchanger and rises above its reach.

In a preferred embodiment, the temperature of the bed of ion exchange resin is increased in the step of desorption by injecting warm water directly into said bed. Typically, the bed of ion exchange resin will be warmed to a temperature of 20-100° C., preferably 40-70° C., at atmospheric pressure.

Preferentially, the temperature of the bed of ion exchange resin is lowered antecedently to the adsorption/absorption step of introducing a stream of gas by injecting cold water directly into said bed. Usually, the ion exchanger bed will be cooled to a temperature of −20-20° C., often 0-10° C., for choice approximately 5° C. However, when used for cleaning of a flue gas, the resin will oftentimes be at more than 30° C.

Moreover, the cooling and heating of the bed of ion exchange resin may be assisted by one or more heat exchangers in the form of a mantle encircling the bed of ion exchange resin or elements protruding into said bed.

In a preferred embodiment, the step of introducing the stream of gas into the bed of weakly basic ion exchange resin provided with amine groups is performed at a pressure of 2 bars (corresponding to 0.2 MPa and being about 1 bar above atmospheric pressure) or more, especially 2.5 bars or more, chiefly 3 bars or more, principally 4 bars or more, favourably 5 bars or more, notably 6 bars or more, advantageously 7 bars or more, particularly 8 bars or more, preferentially 9 bars or more, more preferred 10 bars or more, most preferred 16 bars. In this way, the capacity of the ion exchanger for adsorption of carbon dioxide is significantly augmented.

According to a further embodiment, the bed of ion exchange resin may be supplemented by additional similar beds arranged in a serial array of two or more vessels, between which pressure equalization is applied, so that a gas pressure released from one bed is subsequently utilized in one or more other beds.

BRIEF DESCRIPTION OF THE DRAWING

In the following, a preferred embodiment of the invention will be illustrated with reference to the non-limiting FIGURE which shows a schematic view of a plant carrying out the method according to the invention. Process streams for different phases of the method are indicated.

DETAILED DESCRIPTION OF THE INVENTION

Referring now to the FIGURE, the main features of the illustrated plant are referenced by numbers as follows:

1 is a vessel containing ion exchange resin and water; 2 is a vessel for cold water; and 3 is a vessel for warm water. A shows the phase of cooling the content of vessel 1 with cold water from vessel 2; B illustrates the phase, wherein gas is introduced to the bottom of vessel 1, carbon dioxide is captured, while methane passes through the bed of ion exchange resin and water and is led out from the top of said vessel; C indicates the phase, wherein methane with a higher content of carbon dioxide than accepted exits the bed of ion exchange resin and water and is led to a storage vessel (not shown) for subsequent reprocessing; and D presents the regeneration phase, wherein warm water from vessel 3 is led to vessel 1 such as to increase the temperature of its contents, whereby carbon dioxide is desorbed and is subsequently led out from vessel 1.

A description of a preferred embodiment of the method according to the invention as carried out in the plant of the FIGURE will now be given.

A stream of biogas, which is derived from anaerobic digestion of manure and energy crops, or alternatively originates from wastewater treatment plants, landfills or the like, is passed through a column of activated carbon impregnated with potassium iodide to extensively remove hydrogen sulphide from the biogas. Alternatively, another type of gas in which carbon dioxide is to be separated from at least methane, could have been used in lieu of biogas.

Vessel 1 is prepared for adsorption by cooling the ion exchanger to 5° C. by injection of cold water from vessel 2. When the resin has been cooled, vessel 1 is drained to the point, at which the content of water in the bed of ion exchange resin amounts to approximately 50% of the total weight of ion exchange resin and water.

After having been cleansed from hydrogen sulphide, the biogas is introduced at 5° C. and 100% relative humidity to the bottom of vessel 1 at a pressure of 2 bars (1 bar above atmospheric pressure) and a flow rate of 15 bed volumes per hour. The biogas is mainly composed of carbon dioxide and methane in a ratio of 40/60. Carbon dioxide is absorbed in the water and adsorbed to the ion exchange resin, and methane of a high purity is led out of a valve (not shown) in the top of vessel 1. The pressure is kept constant at 1.5-2 bars.

Without wishing to be bound by a specific theory, it is assumed that the observed propitious synergy of carbon dioxide absorption and adsorption owes itself to the fact that the water acts as a mediator between carbon dioxide in its gas phase and the solid adsorbent resin.

The content of carbon dioxide in the methane leaving the valve in the top of vessel 1 is continuously monitored. When the bed of ion exchange resin and water is saturated at 25-30 bed volumes, the supply of biogas is stopped and any methane with a content of carbon dioxide exceeding the stipulated limit value is led to a storage vessel for subsequent repurification.

Now, vessel 1 is prepared for desorption by draining off the water con-tained therein. The pressure is slowly regulated to atmospheric pressure and vessel 1 is heated from 5° C. to 70° C. by injection of water with a temperature of 70-80° C. from vessel 3. During the heating process adsorbed $CO_2$ is released from the bed of ion exchanger, and carbon dioxide of a high purity is collected from the outlet in the top of vessel 1.

When desorption is substantially complete, the bed of ion exchange resin is ready for being prepared for adsorption as initially described.

The resulting upgraded biogas in the form of almost pure methane may be subjected to drying in a gas drying system and possibly compression as required by the end users, while the separated carbon dioxide may be utilized in various enterprises, e.g. greenhouses or breweries.

EXAMPLES

Example 1

Purity of Upgraded Biogas

A stream of biogas containing 40% $CO_2$ and 60% $CH_4$ is treated according to the method of the invention. The employed ion exchanger is a macroporous polystyrene resin cross-linked with divinylbenzene and the functional group is a tertiary amine. The biogas is introduced at 5° C. and a pressure of 2 bars to the bottom of a bed consisting of ion exchanger and 50% water by weight. Methane at a purity of 98% is obtained. Desorption takes place at 70° C. and atmospheric pressure upon saturation of the bed of ion exchanger.

Example 2

Effect of Relative Water Content on Adsorption Capacity and Adsorption Rate

The adsorption at 5° C. and 2 bars pressure of pure carbon dioxide to a bed of weakly basic, macroporous polystyrene resin cross-linked with divinylbenzene and a tertiary amine as functional group was investigated at varying relative contents of water in said bed. The results are rendered in Table 1.

TABLE 1

| % water by weight in ion exchanger bed | Adsorbed bed volumes of carbon dioxide after 30 minutes |
| --- | --- |
| 0 | 5 |
| 15 | 9 |
| 26 | 12 |
| 55 | 22 |

At all investigated water levels, the adsorption initially went fast and for the levels 0-26% stabilized close to the values indicated above. However, in the bed having a water content of 55% adsorption continued and rose to more than 30 bed volumes of carbon dioxide. It appears that the adsorption capacity as well as the adsorption rate find their optima at a water content in the ion exchange bed of about 50%.

Example 3

Pressure Dependency of Adsorption of $CO_2$

The adsorption at 20° C. of carbon dioxide from a stream of natural gas to a bed of macroporous polystyrene ion exchange resin cross-linked with divinylbenzene and a tertiary amine as functional group (Dowex Marathon WBA-2) was investigated at varying pressures in the vessel containing said bed of ion exchange resin. The content of water in the ion exchange bed amounted to approximately 50% by weight. The results are given in Table 2.

TABLE 2

| Pressure in vessel containing ion exchange resin (bars) | Adsorbed bed volumes of carbon dioxide after 45 minutes |
| --- | --- |
| 1.5 | 16 |
| 2.0 | 27 |
| 2.5 | 35 |
| 10.0 | 53 |
| 16.0 | 59 |

Regeneration of the ion exchanger following adsorption of carbon dioxide was effected at atmospheric pressure by gradual heating of the ion exchanger from 20 to 80° C. in the course of 25 minutes. When adsorption took place at 2.5 bars, more than 28 bed volumes of $CO_2$ (>80%) could be recovered.

By way of comparison, within the interval of 1.5-2.5 bars it was found that in the bed of ion exchanger suffused with water in a proportion of approximately 50% by weight as specified above, 19 additional bed volumes of $CO_2$ was adsorbed for every one bar of pressure increase, whereas in water alone, likewise at 20° C., only 0.7 additional liter of carbon dioxide could be absorbed per liter of water for each incremental pressure of one bar.

As a representative of a gel type resin, Lewatit A 8075 KR, a weakly basic ion exchanger based on an acrylic copolymer with polyamine functional groups, was tested in the same manner. The resin showed a similar adsorption capacity and pressure dependence, although it did only to a scanty de-gree lend itself to regeneration by heating.

Example 4

Separation of $CO_2$ from Flue Gas

A stream of flue gas emanating from a power plant and comprising $N_2$ as a main constituent is freed from most of its contents of $H_2S$, $SO_2$ and $NO_x$ by conventional procedures, and is subseqently purified according to the method of the invention. The content of water in the bed of ion exchanger is approximately 50% by weight, and almost 100% of the $CO_2$ present in the flue gas is scavenged. Compared to a conventional method relying on absorption of $CO_2$ in MEA (monoethanol amine), the energy consumption required for the separation and recovery of each kg of carbon dioxide (in a traditional MEA process around 1 kWh/kg $CO_2$) is reduced by 50-70%. This is partly due to the fact that the perfused bed of ion exchanger presents a lower heat capacity than MEA. Moreover, carbon dioxide is more firmly attached to MEA and more energy is therefore required to strip off $CO_2$ from MEA than to recover $CO_2$ by regeneration of the bed of ion exchanger according to the method of the invention.

The invention claimed is:

1. A method for upgrading or cleaning a gas by separation of carbon dioxide therefrom, comprising the steps of
   introducing a stream of said gas into a bed of a weakly basic ion exchange resin provided with tertiary amine groups, at temperature and pressure conditions, under which the carbon dioxide is adsorbed to said resin, and
   desorbing the adsorbed carbon dioxide from the resin by increasing the temperature and/or lowering the pressure in said bed,
   wherein the content of water in said bed of ion exchange resin during step i) amounts to more than 35% of the total weight of ion exchange resin and water.

2. The method according to claim 1, wherein the gas is flue gas, which is cleaned.

3. The method according to claim 1, wherein the gas is upgraded by separation of carbon dioxide from methane.

4. The method according to claim 3, wherein the gas is biogas.

5. The method according to claim 1, wherein the content of water in said bed of ion exchange resin during step i) amounts to 50% or more of the total weight of ion exchange resin and water.

6. The method according to claim 1, wherein the content of water in said bed of ion exchange resin during step i) amounts to less than 70% of the total weight of ion exchange resin and water.

7. The method according to claim 1, wherein during step i) a flow of water counter to the stream of gas is provided for.

8. The method according to claim 1, wherein the temperature of the bed of ion exchange resin is increased in step ii) by injecting warm water directly into said bed.

9. The method according to claim 1, wherein the temperature of the bed of ion exchange resin is lowered prior to step i) by injecting cold water directly into said bed.

10. The method according to claim 1, wherein cooling and heating of the bed of ion exchange resin is assisted by one or more heat exchangers in the form of a mantle encircling the bed of ion exchange resin or elements protruding into said bed.

11. The method according to claim 1, wherein step i) is performed at a pressure of 2 bars or more.

12. The method according to claim 1, wherein step i) is performed at a pressure of 10 bars or more.

13. The method according to claim 1, wherein step i) is performed at a pressure of 16 bars.

* * * * *